(12) United States Patent
Fang et al.

(10) Patent No.: US 11,051,881 B2
(45) Date of Patent: Jul. 6, 2021

(54) LASSO CATHETER WITH MOVEABLE ABLATION SPINE

(71) Applicant: Biosense Webster (Israel) Ltd., Yokneam (IL)

(72) Inventors: Itzhak Fang, Irvine, CA (US); Jeffrey Clark, Castaic, CA (US); Keshava Datta, Chino Hills, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/895,865

(22) Filed: Jun. 8, 2020

(65) Prior Publication Data

US 2020/0297419 A1    Sep. 24, 2020

Related U.S. Application Data

(62) Division of application No. 14/881,524, filed on Oct. 13, 2015, now Pat. No. 10,687,890.

(51) Int. Cl.
*A61B 18/14* (2006.01)
*A61B 5/287* (2021.01)
*A61B 18/00* (2006.01)

(52) U.S. Cl.
CPC .......... *A61B 18/1492* (2013.01); *A61B 5/287* (2021.01); *A61B 2018/00214* (2013.01);
(Continued)

(58) Field of Classification Search
CPC ........ A61B 18/1492; A61B 2018/1407; A61B 2018/141; A61B 2018/1417; A61B 2018/142; A61B 2018/1465; A61B 2018/1467; A61B 2018/1475; A61B 2018/00577; A61B 2018/00636;
(Continued)

(56) References Cited

U.S. PATENT DOCUMENTS 5,391,199 A    2/1995  Ben-Haim
5,487,385 A    1/1996  Avitall
(Continued)

FOREIGN PATENT DOCUMENTS

EP    2915499 A1    9/2015
WO    1996005768    2/1996
(Continued)

OTHER PUBLICATIONS

Examination Report for European Patent Application No. 16192025.1, dated Nov. 14, 2018.
(Continued)

*Primary Examiner* — Thomas A Giuliani
(74) *Attorney, Agent, or Firm* — Dergosits & Noah LLP; Todd A. Noah (57) ABSTRACT

This disclosure is directed to a method for providing electrical communication with a heart using a catheter having a lasso electrode assembly with a moveable spine. The lasso electrode assembly may have an array of sensing electrodes and may be configured to engage the ostium of the vessel of a patient. The moveable spine may have an ablation electrode and may travel along track around the circumference of the lasso electrode assembly. By adjusting the position of the moveable spine, tissue may be ablated to form lesions around a circumference of the vessel.

8 Claims, 4 Drawing Sheets

(52) U.S. Cl.
CPC ............... *A61B 2018/00375* (2013.01); *A61B 2018/00577* (2013.01); *A61B 2018/00791* (2013.01); *A61B 2018/00821* (2013.01); *A61B 2018/141* (2013.01); *A61B 2018/142* (2013.01); *A61B 2018/1407* (2013.01); *A61B 2018/1467* (2013.01); *A61B 2217/007* (2013.01); *A61B 2218/002* (2013.01)

(58) Field of Classification Search
CPC ........... A61B 2018/00791; A61B 2018/00839; A61B 2018/00375; A61B 2018/00214; A61B 5/287
USPC ........ 606/34, 38, 41, 42, 45, 49; 607/98, 99, 607/101, 113, 115, 116, 119, 122
See application file for complete search history.

(56) References Cited

U.S. PATENT DOCUMENTS

| | | | |
|---|---|---|---|
| 5,738,683 A * | 4/1998 | Osypka | A61L 29/02 606/47 |
| 5,782,899 A | 7/1998 | Imran | |
| 5,997,536 A * | 12/1999 | Osswald | A61B 18/1492 600/374 |
| 6,064,905 A | 5/2000 | Webster et al. | |
| 6,239,724 B1 | 5/2001 | Doron | |
| 6,332,089 B1 | 12/2001 | Acker | |
| 6,484,118 B1 | 11/2002 | Govari | |
| 6,618,612 B1 | 9/2003 | Acker | |
| 6,690,963 B2 | 2/2004 | Ben-Haim | |
| 6,939,349 B2 * | 9/2005 | Fleischman | A61B 18/1492 600/374 |
| 7,435,248 B2 | 10/2008 | Taimisto et al. | |
| 7,591,817 B2 | 9/2009 | Johnson | |
| 8,641,704 B2 | 2/2014 | Werneth et al. | |
| 2002/0065455 A1 | 5/2002 | Ben-Haim | |
| 2003/0120150 A1 | 6/2003 | Govari | |
| 2004/0068178 A1 | 4/2004 | Govari | |
| 2004/0082948 A1 * | 4/2004 | Stewart | A61B 18/1492 606/41 |
| 2005/0070887 A1 * | 3/2005 | Taimisto | A61B 18/1492 606/41 |
| 2008/0294154 A1 * | 11/2008 | Ibrahim | A61B 18/1492 606/13 |
| 2010/0168548 A1 | 7/2010 | Govari | |
| 2013/0299577 A1 | 11/2013 | Bek et al. | |

FOREIGN PATENT DOCUMENTS

| | | |
|---|---|---|
| WO | 20020094115 | 11/2002 |
| WO | 20140036163 | 3/2014 |

OTHER PUBLICATIONS

Search Report from European Patent Application No. 16192025.1, dated Mar. 15, 2017.

* cited by examiner

LASSO CATHETER WITH MOVEABLE ABLATION SPINE

CROSS-REFERENCES TO RELATED APPLICATIONS

This application is a divisional of U.S. patent application Ser. No. 14/881,524, filed Oct. 13, 2015, now U.S. Pat. No. 10,687,890, issued Jun. 23, 2020, which is incorporated herein by reference in its entirety.

FIELD OF THE PRESENT DISCLOSURE

This invention relates to electrophysiologic (EP) catheters, in particular, EP catheters for mapping and/or ablation in the heart.

BACKGROUND

Cardiac arrhythmia, such as atrial fibrillation, occurs when regions of cardiac tissue abnormally conduct electric signals to adjacent tissue, thereby disrupting the normal cardiac cycle and causing asynchronous rhythm. Important sources of undesired signals are located in the tissue region along the pulmonary veins of the left atrium and in the superior pulmonary veins. In this condition, after unwanted signals are generated in the pulmonary veins or conducted through the pulmonary veins from other sources, they are conducted into the left atrium where they can initiate or continue arrhythmia.

Procedures for treating arrhythmia include surgically disrupting the origin of the signals causing the arrhythmia, as well as disrupting the conducting pathway for such signals. More recently, it has been found that by mapping the electrical properties of the endocardium and the heart volume, and selectively ablating cardiac tissue by application of energy, it is sometimes possible to cease or modify the propagation of unwanted electrical signals from one portion of the heart to another. The ablation process destroys the unwanted electrical pathways by formation of non-conducting lesions. An example of such ablation procedures is termed pulmonary vein isolation, and involves the ablation of tissue in the area adjacent the junction of the pulmonary veins and the left atrium. The resulting lesion(s) may isolate irregular electrical signals originating in the area from spreading through the rest of the atrium and disrupting the patient's heart beat.

For these and other applications, conventional practice may involve a two-step procedure. First, a mapping catheter having one or more electrodes for sensing electrical activity is used to measure electrical activity at the treatment area to identify target regions for ablation. In turn, an ablation catheter may then be positioned adjacent the target regions to deliver sufficient energy to form the non-conducting lesions. Accordingly, it would be desirable to provide a catheter and a technique for mapping and ablating tissue without the need to employ multiple catheters. Likewise, it would be desirable it reduce or avoid the need to reposition a catheter while performing mapping and ablation procedures. As will be described in the following materials, this disclosure satisfies these and other needs.

SUMMARY

The present disclosure is directed to a catheter with an elongated catheter body having proximal and distal ends and at least one lumen therethrough and a lasso electrode assembly at the distal end of the catheter body, the lasso electrode assembly having a plurality of sensing electrodes and a moveable spine with an ablation electrode.

In one aspect, the lasso electrode assembly may have a track extending around at least a portion of an inner circumference and the moveable spine may travel along the track. The moveable spine may be secured to a puller member this is disposed within the lumen of the elongated catheter body and extends to a proximal end of the catheter. An actuator at the proximal end of the catheter may be coupled to the puller member, such that manipulation of the actuator adjusts the position of the moveable spine along the track.

In one aspect, the lasso electrode assembly may lie in a plane that is relatively transverse with respect to a longitudinal axis of the elongated catheter body and the moveable spine may curve proximally relative to the plane of the lasso electrode assembly.

In one aspect, the lasso electrode assembly may be configured to engage tissue within an ostium of a vessel of a patient. The moveable spine may have a predetermined shape configured to cause the ablation electrode to contact tissue when the lasso electrode assembly is engaged in the ostium. For example, the vessel may be a pulmonary vein.

In one aspect, the ablation electrode may be irrigated.

In one aspect, the moveable spine may include a temperature sensor.

In one aspect, the elongated catheter body may be steerable.

This disclosure is also directed to a method for providing electrical communication with a heart by providing a catheter having elongated catheter body with proximal and distal ends and at least one lumen therethrough and a lasso electrode assembly at the distal end of the catheter body, the lasso electrode assembly having a plurality of sensing electrodes and a moveable spine with an ablation electrode, positioning the distal end of the catheter at a desired region of the heart and engaging the lasso electrode assembly within an ostium of a vessel to bring at least one of the sensing electrodes into contact with tissue.

In one aspect, providing electrical communication may include recording electrical data received from the at least one electrode in contact with tissue.

In one aspect, the moveable spine may be positioned so that the ablation electrode is in contact with tissue and radio frequency energy may be delivered to the ablation electrode to ablate the tissue and form a lesion. The position of the moveable spine may be adjusted so that the ablation electrode contacts a different tissue region and radio frequency energy may be delivered to the ablation electrode to ablate the tissue and form another lesion. Lesions may be formed lesions around a circumference of the vessel.

In one aspect, the moveable spine may be positioned so that the ablation electrode is in contact with tissue, radio frequency energy may be delivered to the ablation electrode and the position of the moveable spine may be adjusted while delivering radiofrequency energy to ablate the tissue and form a continuous lesion. At least one continuous lesion may be formed around at least a portion of the circumference of the vessel.

In one aspect, positioning the distal end of the catheter at a desired region of the heart may include advancing the lasso electrode assembly from a left atrium through an ostium and into a pulmonary vein.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Certain types of electrical activity within a heart chamber are not cyclical. Examples include arterial flutter or arterial fibrillation, and ventricular tachycardia originating in scars in the wall of the ventricle that have resulted from infarcts. Such electrical activity is random from beat to beat. To analyze or 'map' this type of electrical activity, it is desirable to provide an array of electrodes to provide measurements across a desired area. Conventional lasso catheters have been used to access tissue along an arc surrounding an anatomical structure, such as the ostium of a pulmonary vein. However, electrode designs that are optimized for sensing electrical activity are generally not effective for ablating tissue. Similarly, electrodes designed for ablation may not offer a desired degree of sensitivity when measuring electrical activity or may have decreased maneuverability and/or increased spatial requirements to provide functions related to ablation, such as irrigation and/or temperature sensing. As will be described herein, this disclosure is directed to a lasso catheter having a moveable spine with at least one ablation electrode.

Figure 1:
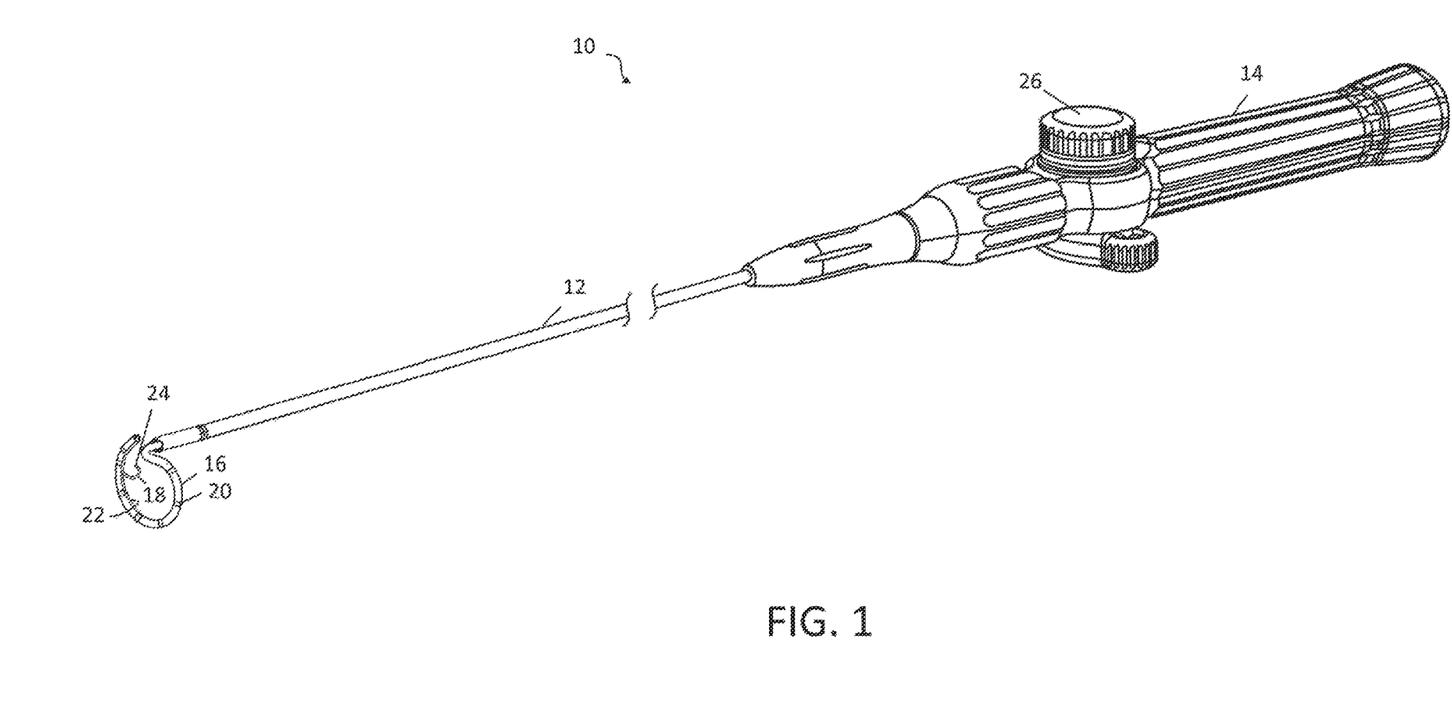
FIG. 1 is a schematic elevational view of a catheter with a lasso electrode assembly having a moveable spine, according to one embodiment.

An exemplary embodiment of a lasso catheter with moveable spine is shown schematically in FIG. 1. Catheter 10 comprises an elongated catheter body 12 having proximal and distal ends and a control handle 14 at the proximal end of the catheter body, with a lasso electrode assembly 16 having a moveable spine 18 at the distal end. Lasso electrode assembly 16 may form a generally known or range-restricted angle that is substantially transverse to the longitudinal axis of catheter body 12. Lasso electrode assembly 16 may be a discrete element that is joined to catheter body 12 or may comprise an extension of catheter body 12. Lasso electrode assembly 16 may be of a known fixed length, and comprises material that preferably is twistable but not stretchable when subjected to typical forces. In one aspect, lasso electrode assembly 16 may be sufficiently resilient so as to assume a predetermined, curved form, when no force is applied thereto, and to be deflected from the predetermined curved form when a force is applied thereto. For example, lasso electrode assembly 16 may have an elasticity that is generally constant over at least a portion of its length, for example, because of internal reinforcement of the curved section with a resilient longitudinal member, as is known in the art. Lasso electrode assembly 16 may form a complete or partial lasso, i.e., as a preformed arcuate structure, which typically subtends between 180° and 360°. In one aspect, lasso electrode assembly 16 may form a substantially complete circle so as to allow mapping and/or ablation around or substantially around the circumference of a vessel. The radius of curvature of lasso electrode assembly 16, when unconstrained, may be typically between 7.5 mm and 15 mm Because the arc structure is resilient and, possibly, slightly helical, when lasso electrode assembly 16 is positioned in the heart (against the ostium of pulmonary vein 50, for example), it will press against the heart tissue over the entire length of the arc, thus facilitating good tissue contact. The arcuate and possibly helical shape of lasso electrode assembly 16 may be maintained, for example, by incorporating a thin strut made from a shape memory material, such as Nitinol as described below.

To enable accurate mapping of electrical signals, lasso electrode assembly 16 may have an array of sensing electrodes 20. Sensing electrodes 20 may be configured as ring electrodes modified to accommodate track 22 as necessary, raised protuberant electrodes such as described in U.S. Patent Application Publication 2010/0168548, the entire disclosure of which is hereby incorporated by reference, or any other suitable design, and may incorporate any suitable number such as ten, twenty or others. Electrodes 20 may be evenly distributed along lasso electrode assembly 16 or may be skewed in any distribution along the arc to facilitate analysis of the measured electrical signals. Electrodes 20 may include a tip electrode as well as electrodes distributed along lasso electrode assembly 16. Typically, electrodes 20 have a width between 1 mm and 4 mm, and are spaced between 1 mm and 10 mm apart.

Moveable spine 18 travels around the arc of lasso electrode assembly 16 within track 22 and may have one or more ablation electrodes, such as electrode 24 which is disposed at the distal end. Moveable spine 18 may also have a preformed shape configured to create a desired degree of contact with tissue to be ablated when lasso electrode assembly 16 is engaged with a target region of the patient's heart, such as within the ostium of a pulmonary vein or other vessel or structure. The shape may also be configured to contact tissue at a desired location relative to lasso electrode assembly 16. For example, moveable spine 18 may curve proximally with respect to lasso electrode assembly 16 as shown. Other shapes may be employed to access different target areas. By positioning moveable spine 18 at multiple locations along track 22, a lesion may be formed by delivering energy through electrode 24 to corresponding locations of the patient's heart. As such, when lasso electrode assembly 16 is positioned within the ostium of a vessel such as a pulmonary vein, moveable spine 18 may be repositioned around the circumference of the vessel through movement within track 22, thereby avoiding the need to move the entire catheter. In this manner, a substantially complete lesion may be formed around the circumference of the vessel to electrically isolate it.

The catheter body 12 is flexible, i.e., bendable, but substantially non-compressible along its length. The catheter body 12 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 12 so that, when the control handle 14 is rotated, the distal end of the catheter body will rotate in a corresponding manner Control handle 14 may also have a rotating knob 26 for adjusting the position of moveable spine 18 along track 22 as described below. In some embodiments, catheter body 12 may be steerable and/or deflectable using any suitable technique, which are known to those of ordinary skill in the art. The outer diameter of the catheter body 12 is not critical, but generally should be as small as possible and may be no more than about 10 french depending on the desired application. For example, for use in the mapping and ablation for isolation of a pulmonary vein, catheter body may have an outer diameter of about 7 to 7.5 french. Likewise the thickness of the outer wall is not critical, but may be thin enough so that the central lumen can accommodate a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

Figure 2:
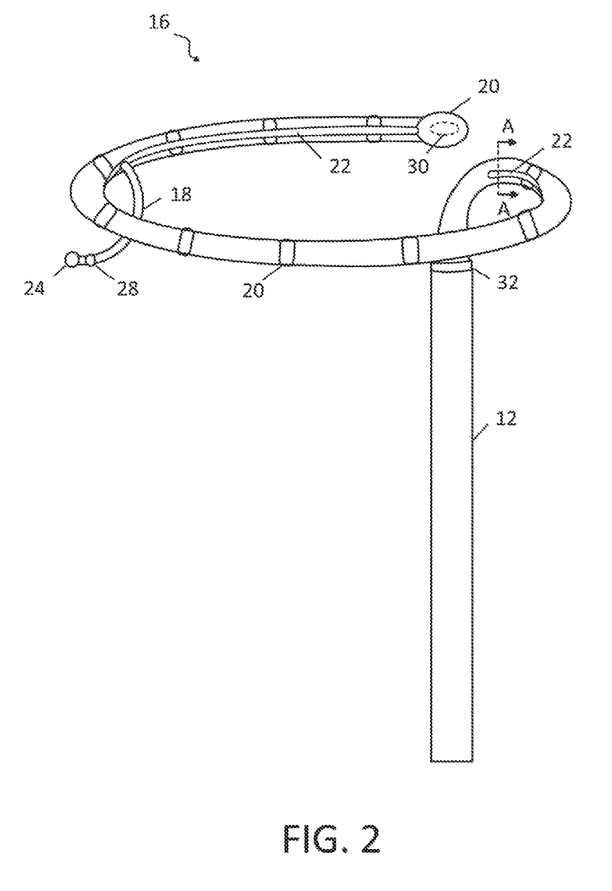
FIG. 2 is a more detailed schematic view of the lasso electrode assembly of FIG. 1, according to one embodiment.

Further details regarding lasso electrode assembly 16 are shown in FIG. 2. As illustrated, track 22 extends around at least a portion of the inner circumference of lasso electrode assembly 16, allowing moveable spine 18 to be positioned at varying locations. As noted, the distal end of moveable spine 18 may have electrode 24 configured to ablate tissue. In some embodiments, electrode 24 may have perforations to allow for the delivery of irrigation fluid to the treatment site to help manage the temperature of the tissue be ablated. During delivery of RF current to electrode 24, heating of the tissue occurs due to its electrical resistance. Heating the tissue causes cellular destruction in the target tissue that results in the formation of the non-conducting lesion that is intended to disrupt the influence of aberrant electrical signals. However, overheating the tissue may cause the undesirable formation of char and coagulum or may result in steam pops when liquid is heated beyond its boiling point, which in turn may create craters or perforations in the heart tissue. Correspondingly, irrigation at the ablation site may provide benefits including cooling of the electrode and tissue to prevent overheating of tissue. Additionally, moveable spine 18 may also have thermocouple 28 or other suitable temperature sensor to assess tissue temperature during an ablation procedure for avoiding such adverse occurrences and to help adjust the flow of irrigation fluid to prevent or minimize overheating. In some embodiments, lasso electrode assembly 16 may include one or more single- or multi-coil position sensors, such as sensors 30 and 32, that may be used as described below to help determine the positioning of catheter 10 within the patient. As illustrated, a first position sensor 30 may be located at the distal end of lasso electrode assembly 16 and a second position sensor may be located at the base of lasso electrode assembly 16 where it joins catheter body 12.

Figure 3:
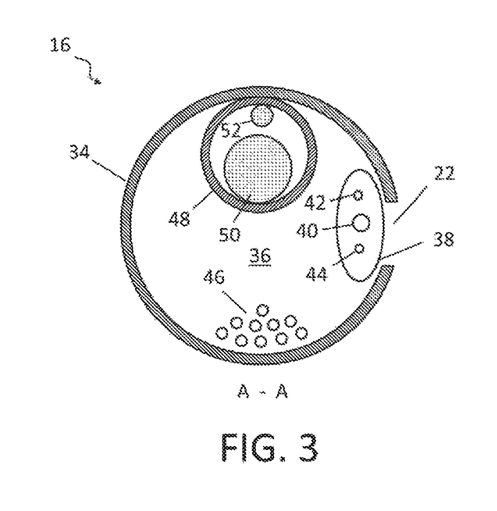
FIG. 3 is a cross section the lasso electrode assembly of FIG. 2 taken at line A-A, according to one embodiment.

Next, FIG. 3 is a cross section taken through line A-A as indicated in FIG. 2. As shown, lasso electrode assembly 16 may be formed from outer tubular member 34 having a slot corresponding to track 22. Disposed within lumen 36 of outer tubular member 34 is puller member 38, to which moveable spine 18 may be secured. Puller member 38 extends to the proximal end of catheter 10 where it is coupled to knob 26. Manipulation of knob 26 extends and retracts puller member 38 within catheter body 12, thereby allowing the position of moveable spine 18 to be adjusted along the length of track 22. As will be appreciated, any suitable configuration of actuator may be provided at the proximal end of catheter 10 to adjust the relative position of moveable spine 18 within track 22, such as a scroll wheel or others. Knob 26 may also feature indicators that reflect the current position of moveable spine and/or recommended distances between ablation points. Embedded within puller member 38 may be irrigation lumen 40 which is in fluid communication with a corresponding lumen within moveable spine 18 to allow irrigation fluid to be delivered to electrode 24. Puller member 38 may also incorporate a lead 42 for electrode 24 and a lead 44 for thermocouple 28 in embodiments having a temperature sensor. Leads 46 for electrodes 20 may also be disposed within lumen 36. In one aspect, an inner tubular member 48 is disposed within lumen 36 and may contain strut 50 as well as a lead 52 for position sensor 30. As noted above, strut 50 may be formed from a resilient material that allows lasso electrode assembly 16 to assume its arcuate shape when freed from constraint. In some embodiments, it may be formed from a suitable shape memory alloy, such as Nitinol or other nickel-titanium alloys, which assumes a remembered shape when heated to physiological temperatures.

Figure 4:
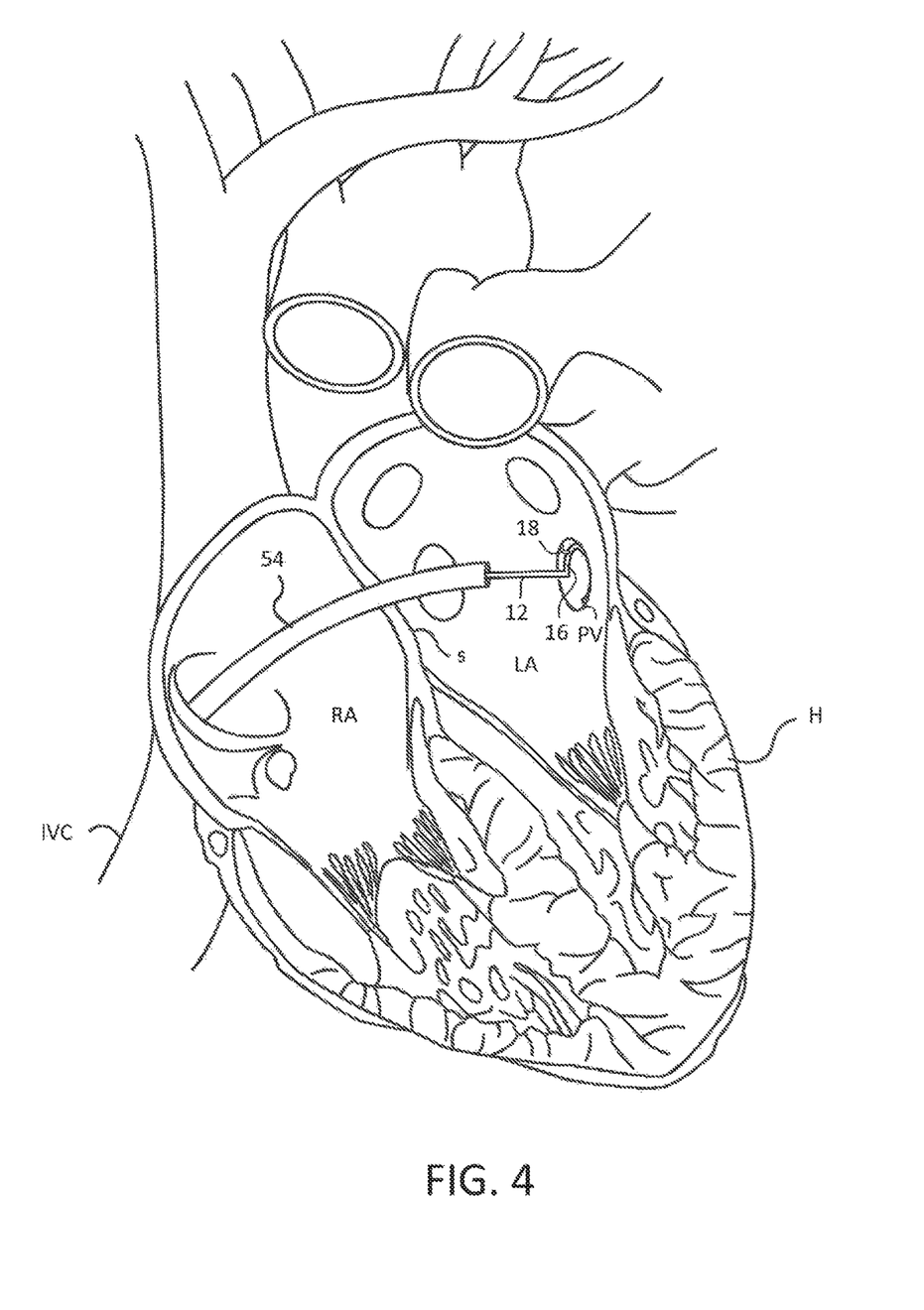
FIG. 4 is a schematic view of the lasso electrode assembly with moveable spine positioned in the ostium of a pulmonary vein, according to one embodiment.

In one aspect, an electrophysiologist may introduce a guiding sheath, guidewire and dilator into the patient, as is generally known in the art. As an example, a guiding sheath for use in connection with the inventive catheter is an appropriately-sized PREFACE™ Braided Guiding Sheath (commercially available from Biosense Webster, Inc., Diamond Bar, Calif.). The guidewire is inserted, the dilator is removed, and the catheter is introduced through the guiding sheath whereby the guidewire lumen in the expander permits the catheter to pass over the guidewire. In one exemplary procedure as depicted in FIG. 4, the catheter is first introduced to the patient's heart (H) through the right atrium (RA) via the inferior vena cava (IVC), where it passes through the septum (S) in order to reach the left atrium (LA).

As will be appreciated, lasso electrode assembly 16, including moveable spine 18, may be deflected into a straightened configuration and constrained within guiding sheath 54 to allow catheter 10 to be passed through the patient's vasculature to the desired location. Once the distal end of the catheter reaches the desired location, e.g., the left atrium, guiding sheath 54 is withdrawn to expose the lasso electrode assembly 16, where it recoils into its arcuate configuration. With the lasso electrode assembly 16 then positioned in the ostium of a pulmonary vein (PV), electrodes 20 contact the ostial tissue and may be used to map electrical signals in this area. Without the need to reposition catheter 10, the electrophysiologist may manipulate knob 26 to adjust the relative position of moveable spine 18 in order to ablate tissue at one or more locations. In some embodiments, it may be desirable to form a substantially complete lesion around the circumference of the pulmonary vein to achieve electrical isolation. This may be achieved by performing multiple ablations that are sufficiently close to each other to overlap or otherwise complete the isolation. Alternatively, energy may be supplied to electrode 24 as moveable spine is repositioned to form a continuous lesion.

Figure 5:
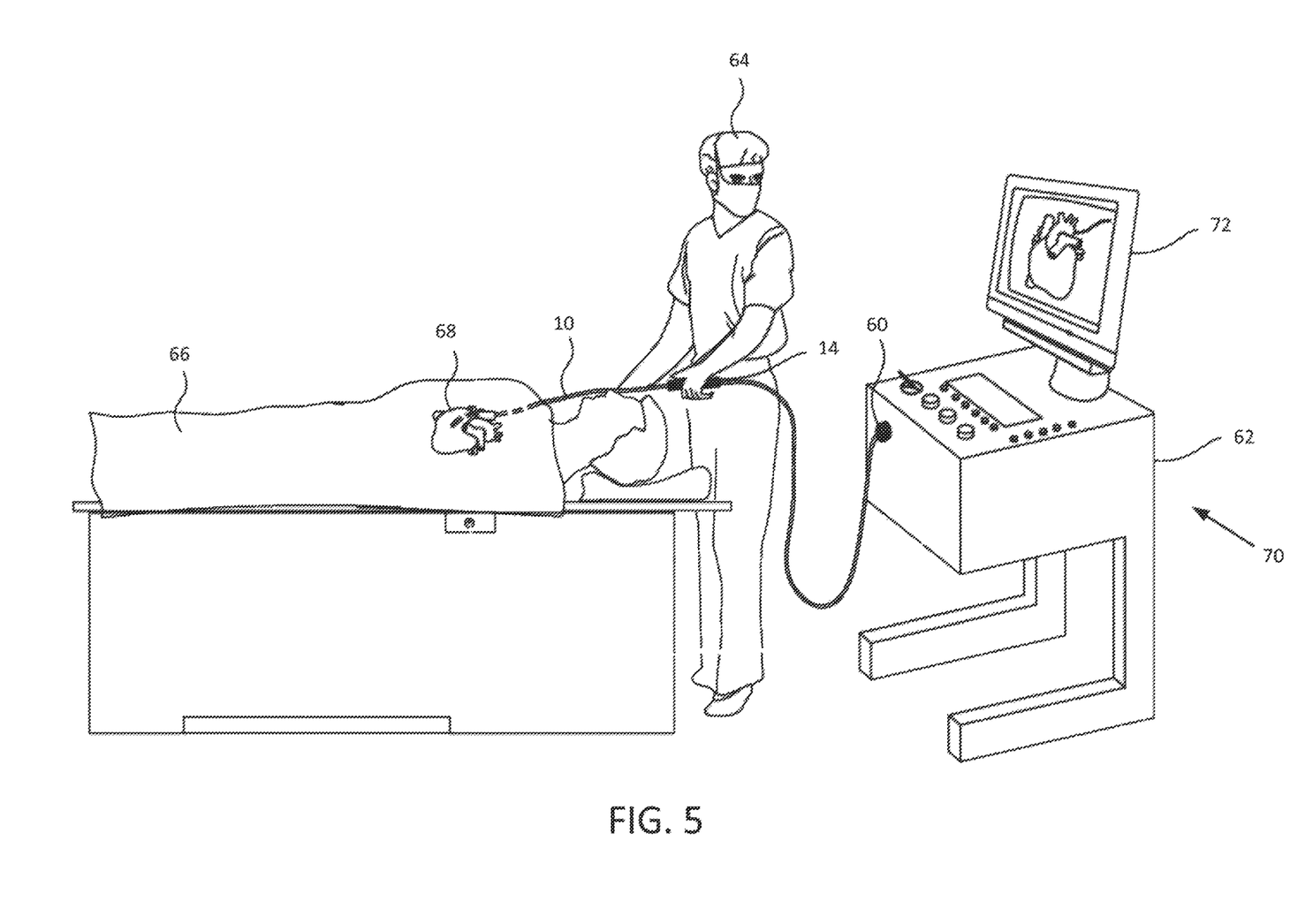
FIG. 5 is a schematic illustration of an invasive medical procedure using a lasso electrode assembly with moveable spine, according to one embodiment.

To help illustrate use of the lasso electrode assembly 16, FIG. 5 is a schematic depiction of an invasive medical procedure, according to an embodiment of the present invention. Catheter 10, with the lasso electrode assembly 16 (not shown in this view) at the distal end may have a connector 60 at the proximal end for coupling the leads 42, 44, 46, 52 and/or others from their respective electrodes and sensors (not shown in this view) to a console 62 for recording and analyzing the signals they detect as well as for supplying ablating energy. An electrophysiologist 64 may insert the catheter 10 into a patient 66 in order to acquire electropotential signals from the heart 68 of the patient. The electrophysiologist 64 uses the control handle 14 attached to the catheter in order to perform the insertion. Console 62 may include a processing unit 70 which analyzes the received signals, and which may present results of the analysis on a display 72 attached to the console. The results are typically in the form of a map, numerical displays, and/or graphs derived from the signals. Processing unit 70 may also control the delivery of energy to electrode 24 for creating one or more lesions. The electrophysiologist 64 may operate knob 26 to adjust the position of moveable spine 18 as indicated above to select where the lesion(s) are formed.

Further, the processing unit 70 may also receive signals from position sensors 30 and 32 (not shown in this view). As noted, the sensor(s) may each comprise a magnetic-field-responsive coil or a plurality of such coils. Using a plurality of coils enables six-dimensional position and orientation coordinates to be determined. The sensors may therefore generate electrical position signals in response to the magnetic fields from external coils, thereby enabling processor 70 to determine the position, (e.g., the location and orientation) of the distal end of catheter 10 within the heart cavity. The electrophysiologist may then view the position of the lasso electrode assembly 16 on an image the patient's heart on the display 72. By way of example, this method of position sensing may be implemented using the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference. As will be appreciated, other location sensing techniques may also be employed. If desired, at least two location sensors may be positioned proximally and distally with lasso electrode assembly 16. The coordinates of the distal sensor relative to the proximal sensor may be determined and, with other known information pertaining to the configuration of lasso electrode assembly 16, used to find the positions of each of the electrodes 20 and/or electrode 24.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A method for providing electrical communication with a heart comprising:
providing a catheter having an elongated catheter body having proximal and distal ends and at least one lumen therethrough and a lasso electrode assembly at the distal end of the catheter body, the lasso electrode assembly having a plurality of sensing electrodes distributed along the lasso electrode assembly, wherein the electrodes are ring electrodes, a track extending around at least a portion of an inner circumference of the lasso electrode assembly, the track defined by an elongated groove in a wall of the inner circumference of the lasso electrode assembly, and a moveable spine extending out from the groove in the wall, the moveable spine having at least one ablation electrode thereon such that the moveable spine travels along the track defined by the elongated groove in the wall of the inner circumference of the lasso electrode assembly;
positioning the distal end of the catheter body at a desired region of the heart; and
engaging the lasso electrode assembly within an ostium of a vessel to bring at least one of the sensing electrodes into contact with tissue.

2. The method of claim 1, wherein providing electrical communication comprises recording electrical data received from the at least one sensing electrode in contact with tissue.

3. The method of claim 1, further comprising positioning the moveable spine so that the ablation electrode is in contact with tissue and delivering radio frequency energy to the ablation electrode to ablate the tissue and form a lesion.

4. The method of claim 3, further comprising adjusting the position of the moveable spine so that the ablation electrode contacts a different tissue region and delivering radio frequency energy to the ablation electrode to ablate the different tissue region and form a lesion.

5. The method of claim 4, further comprising forming lesions around a circumference of the vessel.

6. The method of claim 1, further comprising positioning the moveable spine so that the ablation electrode is in contact with tissue, delivering radio frequency energy to the ablation electrode and adjusting the position of the moveable spine while delivering radiofrequency energy to ablate the tissue and form a continuous lesion.

7. The method of claim 6, further comprising forming at least one continuous lesion around at least a portion of a circumference of the vessel.

8. The method of claim 1, wherein positioning the distal end of the catheter body at the desired region of the heart comprises advancing the lasso electrode assembly from a left atrium into a pulmonary vein.

\* \* \* \* \*